(12) United States Patent
Venugopala et al.

(10) Patent No.: US 12,145,936 B1
(45) Date of Patent: Nov. 19, 2024

(54) 7-IMINO-5-(1H-INDOL-3-YL)-1,3-SUBSTITUTED-7,8-DIHDROPYRIMIDO[4,5-D]PYRIMIDINE-2,4(1H,3H)-DIONE AS ANTI-INFLAMMATORY AGENTS

(71) Applicant: KING FAISAL UNIVERSITY, Al-Ahsa (SA)

(72) Inventors: Katharigatta N. Venugopala, Al-Ahsa (SA); Vinuta Kamat, Bangalore (IN); Rashmi Venugopala, Durban (ZA); Amit Kumar, Bangalore (IN); Boja Poojary, Mangalagangothri (IN)

(73) Assignee: KING FAISAL UNIVERSITY, Al-Ahsa (SA)

( * ) Notice: Subject to any disclaimer, the term of this patent is extended or adjusted under 35 U.S.C. 154(b) by 1 day.

(21) Appl. No.: 18/510,594

(22) Filed: Nov. 15, 2023

(51) Int. Cl.
*C07D 471/04* (2006.01)
(52) U.S. Cl.
CPC .................. *C07D 471/04* (2013.01)
(58) Field of Classification Search
CPC .................................................... C07D 471/04
See application file for complete search history.

(56) References Cited

U.S. PATENT DOCUMENTS

2015/0283248 A1  10/2015  Jayaramareddy et al.

OTHER PUBLICATIONS

Venkatesh et al., Chemical Data Collections (2020), 25, 100335 Coden: CDCHA8; ISSN: 2405-8300.*
Venkatesh et al., Chemical Data Collections (2022), 40, 100886 Coden: CDCHA8; ISSN: 2405-8300.*
PubChem 10 most similar relevant structures to applicants 4b PA0001047.
PubChem 10 most similar relevant structures to applicants 4a PA0001047.
PubChem 10 most similar relevant structures to applicants 4c PA0001047.
Hans Jürgen Solinski et al. ; "Inhibition of natriuretic peptide receptor 1 reduces itch in mice"; Sci Transl Med. Author manuscript; available in PMC May 13, 2020. Published in final edited form as: Sci Transl Med. Jul. 10, 2019; 11(500): eaav5464.
Sunil Kumar et al.; "A brief review of the biological potential of indole derivatives"; Future Journal of Pharmaceutical Sciences vol. 6, Article No. 121 (2020).
Haroon ur Rashid et al. ; "Research developments in the syntheses, anti-inflammatory activities and structure-activity relationships of pyrimidines"; RSC Adv., 2021, 11, 6060; Published online Feb. 3, 2021.
Zienab M. NOFAL1 et al.; "Synthesis of New Pyrimidine Derivatives With Evaluation of Their Anti-Inflammatory and Analgesic Activities"; Acta Poloniae Pharmaceutica—Drug Research, vol. 68 No. 4 pp. 507-517, 2011 ISSN 0001-6837, Polish Pharmaceutical Society.

* cited by examiner

*Primary Examiner* — Paul V Ward
(74) *Attorney, Agent, or Firm* — Nath, Goldberg & Meyer; Joshua B. Goldberg

(57) ABSTRACT

7-Imino-5-(1H-indol-3-yl)-1,3-substituted-7,8-dihydropyrimido[4,5-d]pyrimidine-2,4(1H,3H)-dione derivatives, a method of synthesizing said compounds, a pharmaceutical composition comprising said compounds and a suitable carrier, and a method of using the compounds. The present compounds, identified as COX-2 inhibitors, are useful as anti-inflammatory agents.

17 Claims, No Drawings

7-IMINO-5-(1H-INDOL-3-YL)-1,3-SUBSTITUTED-7,8-DIHDROPYRIMIDO [4,5-D]PYRIMIDINE-2,4(1H,3H)-DIONE AS ANTI-INFLAMMATORY AGENTS

BACKGROUND

1. Field

The present disclosure provides 7-Imino-5-(1H-indol-3-yl)-1,3-substituted-7,8-dihydropyrimido[4,5-d]pyrimidine-2,4(1H,3H)-dione compounds as anti-inflammatory agents, compositions containing such compounds, and method of preparation. These compounds and compositions are useful as therapeutic agents for reducing pain and inflammation.

2. Description of the Related Art

Non-steroidal anti-inflammatory drugs (NSAIDs) have been therapeutically used in the medication of rheumatic arthritis and also in the treatment of various inflammatory disorders. Due to their gastrointestinal side effects, they are often used in limited numbers.

Dihydropyrimidine derivatives are reported for anticancer (Katharigatta N V, Reshme G, Mohammed A K, Rashmi V, Bandar E A, Sree H, et al., Design, synthesis, and computational studies on dihydropyrimidine scaffolds as potential lipoxygenase inhibitors and cancer chemopreventive agents. Drug Design, Development and Therapy 2015; 911-921. doi.org/10.2147/DDDT.S73890), larvicidal against *Anopheles arabiensis* (Ramasamy D, Nizar A A, Sandeep C, Pran K D, Raquel M G, Christophe T, et al., Synthesis, biological evaluation, and computational investigation of ethyl 2,4,6-trisubstituted-1,4-dihydropyrimidine-5-carboxylates as potential larvicidal agents against *Anopheles arabiensis*. Journal of Biomolecular Structure and Dynamics 2023. DOI: 10.1080/07391102.2023.2217929; Katharigatta N V, Pottathil S, Christophe T, Pran K D, Raquel M G, Sandeep C, et al, 1,2,3-Triazolyl-tetrahydropyrimidine Conjugates as Potential Sterol Carrier Protein-2 Inhibitors: Larvicidal Activity against the Malaria Vector *Anopheles arabiensis* and In Silico Molecular Docking Study. Molecules 2023; 27(9):2676. doi.org/10.3390/molecules27092676; Mariela E S, Maria E M, Virginia M, Raquel M G, Bharti O, Katharigatta N V, et al., Membrane effects of dihydropyrimidine analogues with larvicidal activity. Colloids and Surfaces B: Biointerfaces 2017; 150:106-113. doi.org/10.1016/j.colsurfb.2016.11.028; Keshab M B, Katharigatta N V, Pradip K M, Raquel M G, Deepak C, Daniel G, et al., Larvicidal study of tetrahydropyrimidine scaffolds against *Anopheles arabiensis* and structural insight by single crystal X-ray studies. Chemical Biology & Drug Design 2018; 92(6): 1924-1932. doi.org/10.1111/cbdd.13351; Katharigatta N V, Raquel M G, Raju K C, Bharti O. Antimosquito properties of 2-substituted phenyl/benzylamino-6-(4-chlorophenyl)-5-methoxycarbonyl-4-methyl-3, 6-dihydropyrimidin-1-ium chlorides against *Anopheles arabiensis*. Medicinal Chemistry 2014; 10(2):211-219. DOI: 10.2174/15734064102140131164945), polymorphism properties (Katharigatta N V, Susanta K N, Raquel M G, Mariela E S, Daniel A G, Bharti O. Synthesis, Polymorphism, and Insecticidal Activity of Methyl 4-(4-chlorophenyl)-8-iodo-2-methyl-6-oxo-1,6-dihydro-4H-pyrimido[2,1-b]quinazoline-3-carboxylate Against *Anopheles arabiensis* mosquito. Chemical Biology & Drug Design 2016; 88(1):88-96. doi.org/10.1111/cbdd.12736; Piyush P, Katharigatta N V, Bharti O, Deepak C. Polymorphism in two biologically active dihydropyrimidinium hydrochloride derivatives: quantitative inputs towards the energetics associated with crystal packing. Acta Crystallographica Section B: Structural Science, Crystal Engineering and Materials 2014; 70(4):681-696. doi.org/10.1107/S2052520614006209), anthelmintic (Satya S C, Praveen B, Pran K D, Raghu P M, Katharigatta N V, Anroop B N, et al., Synthesis and anthelmintic activity of some novel (E)-2-methyl/propyl-4-(2-(substitutedbenzylidene)hydrazinyl)-5,6,7,8-tetrahydrobenzo[4,5]thieno[2,3-d]pyrimidines. Medicinal Chemistry Research 2020; 29:1600-1610. doi.org/10.1007/s00044-020-02586-5), anti-diabetic (Keshab M B, Nancy S Y, Promise M E, Katharigatta N V, Osama I A, Hany E K, et al., Chemistry, anti-diabetic activity and structural analysis of substituted dihydropyrimidine analogues. Journal of Molecular Structure 2021; 1227:129412. doi.org/10.1016/j.molstruc.2020.129412; Keshab M B, Nancy S Y, Promise M E, Ekta S, Rajesh G G, Katharigatta N V, et al., Antidiabetic activity of dihydropyrimidine scaffolds and structural insight by single crystal x-ray studies. Medicinal Chemistry 2020; 16(7):996-1003. doi.org/10.2174/15734064166661191227123048), and anti-tubercular properties (Katharigatta N V, Christophe T, Melendhran P, Sandeep C, Omar H A, Bandar E A, et al., In silico design and synthesis of tetrahydropyrimidinones and tetrahydropyrimidinethiones as potential thymidylate kinase inhibitors exerting anti-TB activity against *Mycobacterium tuberculosis*. Drug Design, Development and Therapy 2020; 1027-1039. doi.org/10.2147/DDDT.S228381; Katharigatta N V, Rao G B D, Subhrajyoti B, Melendhran P, Deepak C, Bandar E A, et al., Design, synthesis, and characterization of (1-(4-aryl)-1H-1,2,3-triazol-4-yl)methyl, substituted phenyl-6-methyl-2-oxo-1,2,3,4-tetrahydropyrimidine-5-carboxylates against *Mycobacterium tuberculosis*. Drug Design, Development and Therapy 2016:2681-2690. doi.org/10.2147/DDDT.S109760; Katharigatta N V, Susanta K, Melendhran P, Renuka P, Yacoob M C, Bharti O. Synthesis and anti-tubercular activity of 2-(substituted phenyl/benzyl-amino)-6-(4-chlorophenyl)-5-(methoxycarbonyl)-4-methyl-3, 6-dihydropyrimidin-1-ium chlorides. Chemical Biology & Drug Design 2013; 81(2):219-227. DOI: 10.1111/cbdd.12065).

Thus, there exists a need to develop anti-inflammatory agents which may not cause gastrointestinal side effects.

SUMMARY

The present subject matter relates to the use of novel 7-Imino-5-(1H-indol-3-yl)-1,3-substituted-7,8-dihydropyrimido[4,5-d]pyrimidine-2,4(1H,3H)-dione compounds as anti-inflammatory agents to be used in the place of NSAIDs, which are known to cause gastrointestinal problems.

In this regard, the present subject matter relates to a series of 7-Imino-5-(1H-indol-3-yl)-1,3-substituted-7,8-dihydropyrimido[4,5-d]pyrimidine-2,4(1H,3H)-dione as anti-inflammatory agents made by a green synthesis process. In an effort to develop novel anti-inflammatory agents, a series of 7-Imino-5-(1H-indol-3-yl)-1,3-substituted-7,8-dihydropyrimido[4,5-d]pyrimidine-2,4(1H,3H)-dione derivatives have been achieved by a green synthetic method and purified by recrystallization and column chromatographic methods. The compounds can be obtained in good yields using the present advantageous methods. Structural elucidation of the compounds is completed by spectral techniques such as FT-IR, NMR ($^1$H and $^{13}$C), LC-MS, and elemental analysis. These compounds were evaluated for their anti-inflammatory activity and some show promising anti-inflammatory activity between millimolar to micromolar concentrations compared to standard anti-inflammatory drugs. Some of the selected lead compounds can be successfully taken forward to develop novel anti-inflammatory drug candidates.

Accordingly, the present subject matter relates to the use of novel 7-Imino-5-(1H-indol-3-yl)-1,3-substituted-7,8-dihydropyrimido[4,5-d]pyrimidine-2,4(1H,3H)-dione derivatives for inhibiting COX-2 isoenzymes, which are known to cause inflammation in the body. Reducing inflammation can decrease pain, swelling, and illnesses and diseases associated with excess inflammation. The present subject matter further provides a process for the synthesis of such compounds, pharmaceutical compositions containing these compounds, and their use in therapy for inhibiting COX-2 and for treatment of inflammation in a patient, either alone or in combination with other active ingredients.

In an embodiment, the present subject matter relates to a compound having the formula I:

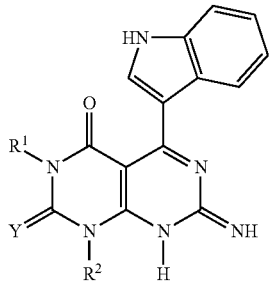

I or a pharmaceutically acceptable salt, ester, stereoisomer, or solvate thereof, wherein:
$R^1$ is selected from the group consisting of hydrogen and methyl;
$R^2$ is selected from the group consisting of hydrogen and methyl; and
Y is selected from the group consisting of O and S.

In another embodiment, the present subject matter relates to a compound having the formula I:

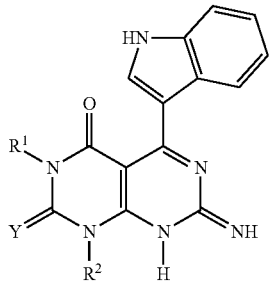

I or a pharmaceutically acceptable salt, ester, stereoisomer, or solvate thereof, wherein:
$R^1$ and $R^2$ are both hydrogen or are both methyl; and
Y is selected from the group consisting of O and S.

In an embodiment, the present subject matter relates to a compound selected from the group consisting of: 7-Imino-5-(1H-indol-3-yl)-7,8-dihydropyrimido[4,5-d]pyrimidine-2,4(1H,3H)-dione (4a), 7-Imino-5-(1H-indol-3-yl)-2-thioxo-2,3,7,8-tetrahydropyrimido[4,5-d]pyrimidin-4(1H)-one (4b), 7-Imino-5-(1H-indol-3-yl)-1,3-dimethyl-7,8-dihydropyrimido[4,5-d]pyrimidine-2,4(1H,3H)-dione (4c), and a pharmaceutically acceptable salt, ester, stereoisomer, or solvate thereof.

In an embodiment, the present subject matter relates to a process for the synthesis of the compounds of formula I, including a number of species or specific structures falling under structural formula I. Further contemplated herein are pharmaceutical compositions containing these compounds, as well as methods of treating inflammation by administering the present compounds to a patient in need thereof.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "halo" or "halogen" refers to fluoro, chloro, iodo, and bromo.

As used herein, "heteroatom" refers to an atom of any element other than carbon or hydrogen and includes, for example, nitrogen, oxygen, silicon, sulfur, phosphorus, and selenium.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

It will be understood by those skilled in the art with respect to any chemical group containing one or more substituents that such groups are not intended to introduce any substitution or substitution patterns that are sterically impractical and/or physically non-feasible.

The term "isomers" or "stereoisomers" as used herein relates to compounds that have identical molecular formulae but that differ in the arrangement of their atoms in space. Stereoisomers that are not mirror images of one another are termed "diastereoisomers" and stereoisomers that are non-superimposable mirror images are termed "enantiomers," or sometimes optical isomers. A carbon atom bonded to four non-identical substituents is termed a "chiral center." Certain compounds herein have one or more chiral centers and therefore may exist as either individual stereoisomers or as a mixture of stereoisomers. Configurations of stereoisomers that owe their existence to hindered rotation about double bonds are differentiated by their prefixes cis and trans (or Z and E), which indicate that the groups are on the same side (cis or Z) or on opposite sides (trans or E) of the double bond in the molecule according to the Cahn-Ingold-Prelog rules. All possible stereoisomers are contemplated herein as individual stereoisomers or as a mixture of stereoisomers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as inflammation.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to a compound having the formula I:

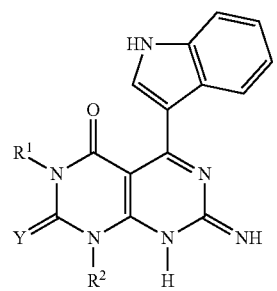

I or a pharmaceutically acceptable salt, ester, stereoisomer, or solvate thereof, wherein:

$R^1$ is selected from the group consisting of hydrogen and methyl;

$R^2$ is selected from the group consisting of hydrogen and methyl; and

Y is selected from the group consisting of O and S.

In one embodiment, $R^1$ and $R^2$ can both be hydrogen. In such embodiments, Y can be O or S.

In another embodiment, $R^1$ and $R^2$ can both be methyl. In such embodiments, Y can be O.

In another embodiment, the present subject matter relates to a compound having the formula I:

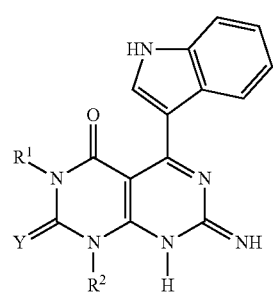

I or a pharmaceutically acceptable salt, ester, stereoisomer, or solvate thereof, wherein:

$R^1$ and $R^2$ are both hydrogen or are both methyl; and

Y is selected from the group consisting of O and S.

In an embodiment, the present subject matter relates to a compound selected from the group consisting of: 7-Imino-5-(1H-indol-3-yl)-7,8-dihydropyrimido[4,5-d]pyrimidine-2,4(1H,3H)-dione (4a), 7-Imino-5-(1H-indol-3-yl)-2-thioxo-2,3,7,8-tetrahydropyrimido[4,5-d]pyrimidin-4(1H)-one (4b), 7-Imino-5-(1H-indol-3-yl)-1,3-dimethyl-7,8-dihydropyrimido[4,5-d]pyrimidine-2,4(1H,3H)-dione (4c), and a pharmaceutically acceptable salt, ester, stereoisomer, or solvate thereof.

Said differently, the present subject matter can relate to compounds of formula I selected from the group consisting of:

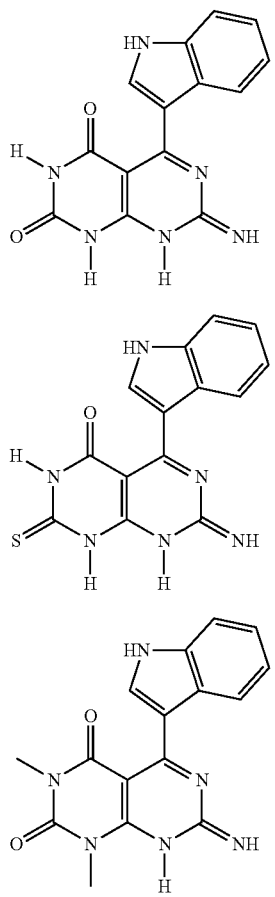

4a

4b

4c and a pharmaceutically acceptable salt, ester, stereoisomer, or solvate thereof.

It is to be understood that the present subject matter covers all combinations of substituent groups referred to herein.

The present compounds may contain, e.g., when isolated in crystalline form, varying amounts of solvents. Accordingly, the present subject matter includes all solvates of the present compounds of formula I and pharmaceutically acceptable stereoisomers, esters, and/or salts thereof. Hydrates are one example of such solvates.

Further, the present subject matter includes all mixtures of possible stereoisomers of the embodied compounds, independent of the ratio, including the racemates.

Salts of the present compounds, or salts of the stereoisomers thereof, include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, D-gluconates, benzoates, 2-(4-hydroxy-benzoyl)benzoates, butyrates, subsalicylates, maleates, laurates, malates, lactates, fumarates, succinates, oxalates, tartrates, stearates, benzenesulfonates (besilates), toluenesulfonates (tosilates), methanesulfonates (mesilates) and 3-hydroxy-2-naphthoates.

Examples of salts with bases include, but are not limited to, lithium, sodium, potassium, calcium, aluminum, magnesium, titanium, ammonium, meglumine and guanidinium salts. The salts include water-insoluble and, particularly, water-soluble salts.

The present compounds, the salts, the stereoisomers and the salts of the stereoisomers thereof may contain, e.g., when isolated in crystalline form, varying amounts of solvents. Included within the present scope are, therefore, all solvates of the compounds of formula I, as well as the solvates of the salts, the stereoisomers and the salts of the stereoisomers of the compounds of formula I.

The present compounds may be isolated and purified in a manner known per se, e.g., by distilling off the solvent in vacuo and recrystallizing the residue obtained from a suitable solvent or subjecting it to one of the customary purification methods, such as column chromatography on a suitable support material.

Salts of the compounds of formula I and the stereoisomers thereof can be obtained by dissolving the free compound in a suitable solvent (by way of non-limiting example, a ketone such as acetone, methylethylketone or methylisobutylketone; an ether such as diethyl ether, tetrahydrofurane or dioxane; a chlorinated hydrocarbon such as methylene chloride or chloroform; a low molecular weight aliphatic alcohol such as methanol, ethanol or isopropanol; a low molecular weight aliphatic ester such as ethyl acetate or isopropyl acetate; or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the present compounds can be obtained, e.g., by asymmetric synthesis, by using chiral starting compounds in synthesis and by splitting up enantiomeric and diastereomeric mixtures obtained in synthesis. Preferably, the pure diastereomeric and pure enantiomeric compounds are obtained by using chiral starting compounds in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated, e.g., by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is enzymatic separation.

In one embodiment, the present compounds can be prepared according to the following general synthetic pathway. Specifically, a mixture of indolyl aldehyde 1 (1 equiv.), substituted barbituric acids (2a and 2c) and thio-barbituric acid 2b derivatives (1 equiv.), and guanidine hydrochloride 3 (1 equiv.) can be taken in a round-bottomed flask. The water:ethanol (8:2, v/v) mixture, along with a catalytic amount of ceric ammonium nitrate (CAN), can then be added thereto. The mixture can then be stirred at ambient temperature for about five hours, or at least about five hours. Completion of the reaction is monitored by TLC (EtOAc: Hexane, 2:8) and the formed product can be filtered, dried, and recrystallized by an ethanol solvent to yield 91-95%.

The synthetic strategy adopted is illustrated in Scheme 1.

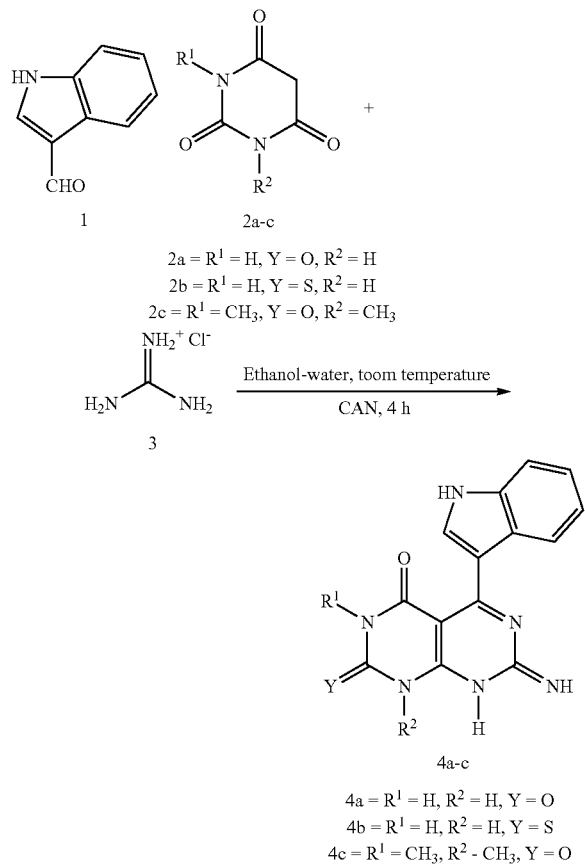

In another embodiment, the present subject matter is directed to pharmaceutical compositions comprising a therapeutically effective amount of the compounds as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises at least one of the present compounds together with at least one pharmaceutically acceptable auxiliary.

In an embodiment, the pharmaceutical composition comprises one, two, or more of the present compounds, or one of the present compounds.

Non-limiting examples of suitable excipients, carriers, or vehicles useful herein include liquids such as water, saline, glycerol, polyethyleneglycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compounds are typically administered at a therapeutically or pharmaceutically effective dosage, e.g., a dosage sufficient to provide treatment for inflammation. Administration of the compounds or pharmaceutical compositions thereof can be by any method that delivers the compounds systemically and/or locally. These methods include oral routes, parenteral routes, intraduodenal mutes, and the like.

While human dosage levels have yet to be optimized for the present compounds, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compounds for treatment of inflammation, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of a compound or salt of the present compounds, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410, 545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid, or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol, or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

The present compounds have valuable pharmaceutical properties, which make them commercially utilizable. Accordingly, the present subject matter further relates to use of the present compounds for the treatment of inflammation and diseases associated with inflammation. Similarly, the present compounds can be used to inhibit COX-2 enzyme activity in a patient. The present compounds may also be used to treat pain and swelling associated with inflammation.

Accordingly, in an embodiment of the present subject matter, the 7-imino-5-(1H-indol-3-yl)-1,3-substituted-7,8-dihydropyrimido[4,5-d]pyrimidine-2,4(1H,3H)-dione derivatives, as described herein engaged for in vitro study towards the human COX-2 isoenzymes can display a mild selective inhibition against COX-2. The inhibitory activity of the tested compounds can be reported as inhibition percentage mean±SEM.

In another embodiment, 10 µM of a present compound engaged for in vitro study can display a COX-2% Inhibition of about 23 to about 98 at an incubation time of at least 18 hours.

In a further embodiment, 10 μM of a present compound, for example, compound (4a), engaged for in vitro study can display a COX-2% Inhibition of 23±5.1 at an incubation time of at least 18 hours.

In an embodiment, 10 μM of a present compound, for example, compound (4b), engaged for in vitro study can display a COX-2% Inhibition of 88±2.91 at an incubation time of at least 18 hours.

In another embodiment, 10 μM of a present compound, for example, compound (4c), engaged for in vitro study can display a COX-2% Inhibition of 98±1.53 at an incubation time of at least 18 hours.

The present subject matter further relates to a method of treating or preventing a disease comprising administering to a patient in need thereof a therapeutically effective amount of at least one of the compounds herein.

In particular, the present subject matter relates to a method of treating one of the above-mentioned diseases or disorders comprising administering to a patient in need thereof a therapeutically effective amount of at least one of the compounds herein.

In the above methods, the patient is preferably a mammal, more preferably a human. Furthermore, in the above methods, at least one of the present compounds can be used. In an embodiment, one, two, or more of the present compounds are used, or one of the present compounds is used. Similarly, one or more of the present compounds can be used in combination therapy with one or more additional active agents.

The following examples relate to various methods of manufacturing certain specific compounds as described herein. All compound numbers expressed herein are with reference to the synthetic pathway figures shown above.

EXAMPLES

Example 1

General Procedure for the Synthesis of 7-imino-5-(1H-indol-3-yl)-1,3-substituted-7,8-dihydropyrimido[4,5-d]pyrimidine-2,4(1H,3H)-dione (4a-c)

A mixture of indolyl aldehyde 1 (1 equiv.), substituted barbituric acids (2a and 2c) and thio-barbituric acid 2b derivatives (1 equiv.), and guanidine hydrochloride 3 (1 equiv.) were taken in a round-bottomed flask. The water:ethanol (8:2, v/v) mixture was added along with catalytic amount of ceric ammonium nitrate (CAN). The reaction medium was stirred at ambient temperature for five hours. Completion of the reaction was monitored by TLC (EtOAc:Hexane, 2:8) and the formed product was filtered, dried, and recrystallized by ethanol solvent, and the yield obtained was 91-95%.

The compounds (4a-c) were prepared following this protocol and the characterization details are reported below.

Example 2

7-Imino-5-(1H-indol-3-yl)-7,8-dihydropyrimido[4,5-]pyrimidine-2,4(1H,3H)-dione (4a)

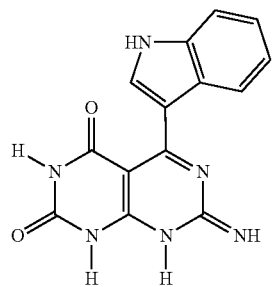 [SMILES: N=c1nc(-c2c[nH]c3ccccc23)c2c(=O)[nH]c(=O)[nH]c2[nH]1]

4a

Yield: 91%; Melting point: 158-160° C.; $^1$H NMR (DMSO-d$_6$, 400 MHz): δ=12.49 (s, 1H, —NH), 10.81 (d, 1H, J=32.4 Hz-indole-NH), 9.96 (s, 1H, —NH), 9.47 (s, 1H, —NH), 8.73 (s, 1H, Ar—H), 8.14 (d, 1H, Ar—H, J=4.2 Hz), 7.87 (d, 1H, Ar—H, J=8.8 Hz), 7.60 (dd, 1H, Ar—H, J=3.6 and 10.0 Hz), 7.33 (dd, 2H, Ar—H, J=1.6 and 19.2 Hz); $^{13}$C NMR (DMSO-d$_6$, 100 MHz): δ=164.5, 163.2, 150.4, 143.7, 139.7, 136.4, 129.1, 123.7, 122.7, 117.6, 113.2, 111.4, 108.6; MS (m/z): 295 [M+H]; Elemental analysis of C$_{14}$H$_{10}$N$_6$O$_2$, Calcd: C: 57.14; H: 3.43; N: 28.56, Found: C: 57.13; H: 3.45; N: 28.57.

Example 3

7-Imino-5-(1H-Indol-3-yl)-2-thioxo-2,3,7,8-tetrahydropyrimido[4,5-d]pyrimidin-4(1H)-one (4b)

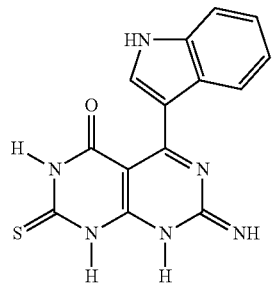

4b

Yield: 92%; Melting point: 178-180° C.; $^1$H NMR (DMSO-d$_6$, 400 MHz): δ=12.26 (s, 1H, —NH), 10.36 (s, 1H, indole-NH), 9.54 (s, 1H, —NH), 8.70 (s, 1H, Ar—H), 7.85 (dd, 1H, Ar—H, J=1.2, 2.8, 6.0 and 7.6 Hz), 7.59 (dd, 1H, Ar—H, J=2.4, 3.0, 6.8 and 12.8 Hz), 7.27 (dd, 1H, Ar—H, J=3.6, 4.4, 28.8 and 29.6 Hz), 6.96-6.81 (m, 2H, Ar—H), 5.66 (s, 1H, —NH); $^{13}$C NMR (DMSO-d$_6$, 100 MHz): δ=177.7, 166.5, 163.1, 144.5, 141.4, 136.8, 135.4, 124.1, 123.1, 117.8, 113.5, 112.5, 108.6, 89.5; MS (m/z): 310 [M]; Elemental analysis of C$_{14}$H$_{10}$N$_6$OS, Calcd: C: 54.18; H: 3.25; N: 27.08, Found: C: 54.19; H: 3.23; N: 27.07.

Example 4

7-Imino-5-(1H-indol-3-yl)-1,3-dimethyl-7,8-dihydropyrimido[4,5-d]pyrimidine-2,4(1H,3H)-dione (4c)

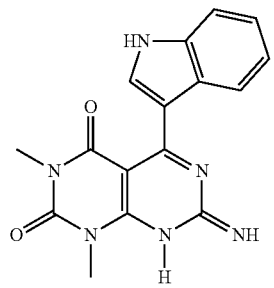

Yield: 95%; Melting point: 266-268° C.; $^1$H NMR (DMSO-$d_6$, 400 MHz): δ=12.79 (s, 1H, —NH), 9.51 (s, 1H, —NH), 8.78 (s, 1H, Ar—H), 7.86 (d, 1H, Ar—H, J=3.6 and 4.8 Hz), 7.59 (d, 1H, Ar—H, J=3.6 and 4.8 Hz), 7.33 (d, 3H, Ar—H, J=4.0 and 4.4 Hz), 3.34 (s, 6H, —CH$_3$); $^{13}$C NMR (DMSO-$d_6$, 100 MHz): δ=163.1, 154.9, 151.2, 144.6, 139.9, 136.4, 129.3, 125.5, 123.7, 122.7, 117.6, 113.2, 111.5, 108.3, 28.4, 27.7; MS (m/z): 322 [M]; Elemental analysis of $C_{16}H_{14}N_6O_2$, Calcd: C: 59.62; H: 4.38; N: 26.07, Found: C: 59.63; H: 4.37; N: 26.05.

Pharmacological Activity

Example 5

Cyclooxygenases (COX-2) Enzyme Inhibition Assay

According to manufacturer instructions, a COX inhibition assay was performed using COX (human) Inhibitor Screening Assay Kit for the compounds 7-imino-5-(1H-indol-3-yl)-1,3-substituted-7,8-dihydropyrimido[4,5-d]pyrimidine-2,4(1H,3H)-dione derivatives (4a-c). All reagents and buffers were prepared in ultrapure water. All stock solutions of the compounds and the positive controls (Indomethacin and Celecoxib) were dissolved in DMSO. In each inhibitor sample tube, 160 μL reaction buffer, 10 μL of heme, 10 μL of diluted COX-2 enzyme, and 10 μL of the diluted inhibitor was added to get a final concentration of 100 μM. The background samples were prepared for COX-2 by heat inactivating the enzymes in boiling water for 3 minutes, and 10 μL of the inactive COX-2 were added to the background tubes. 10 μL of the vehicle control (DMSO) was added to the background tubes, and COX enzyme's 100% initial activity was obtained. All reaction tubes were incubated for 10 minutes at 37° C. Following this incubation, 10 μL of the substrate, arachidonic acid (AA), was added to all test tubes, mixed, and further incubated for precisely 30 seconds at 37° C. Then, 30 μL of SnCl$_2$ solution was added to each reaction tube to stop the enzyme catalysis. All reaction tubes were removed from the incubator, vortexed, and incubated again for 5 min at room temperature. Reaction tubes were stored at 4° C. to quantify the prostaglandin formation by competitive enzyme-linked immunosorbent assay (ELISA). ELISA standards were prepared in test tubes to perform the competitive ELISA, and dilutions were prepared with the ELISA buffer. The standards, COX reaction dilutions, and background samples were serially diluted. After that, 50 μL of the diluted standards, COX background, COX 100% initial activity, and COX inhibitor samples were transferred to the corresponding wells of 96 well ELISA plate. Blank (to assess the background absorbance caused by Ellman's reagent) and total activity (TA) (to determine the enzymatic activity of the AChE-linked tracer) wells were left empty, 100 μL and 50 μL of the ELISA buffer were added to the nonspecific binding (NSB) and maximum binding (B0), respectively. Prostaglandin screening AChE tracer (50 μL) and prostaglandin screening ELISA antiserum (50 μL) were added to corresponding wells except for TA. The plate was covered with a plastic film, wrapped with foil to protect from light, and incubated for 18 hours at room temperature. Following incubation, the plate was washed and developed with 200 μL of Ellman's reagent to all wells, and 5 μL of tracer was added to TA well. The plate was covered with foil, placed on an orbital shaker, and incubated for 60-90 minutes. Finally, the plate reading was done at a wavelength of 405 nm with a Microplate reader from BioTek (by Agilent), and data were collected using Gen5™ (by Agilent) analysis software.

In vitro catalytic inhibition data of compounds 7-imino-5-(1H-indol-3-yl)-1,3-substituted-7,8-dihydropyrimido[4,5-d]pyrimidine-2,4(1H,3H)-dione derivatives (4a-c) at 10 μM against human COX-2 enzyme is listed in Table 1.

TABLE 1

| Compound code | Chemical Structure | % Inhibition (COX-2) Mean ± SEM |
|---|---|---|
| 4a | 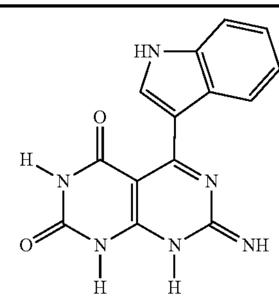 | 23 ± 5.1 |
| 4b | 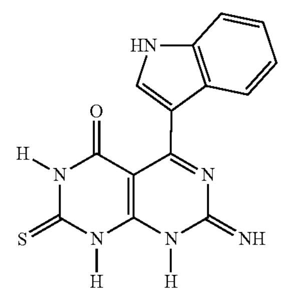 [SMILES: N=c1nc(-c2c[nH]c3ccccc23)c2c(=O)[nH]c(=S)[nH]c2[nH]1] | 88 ± 2.91 |
| 4c | 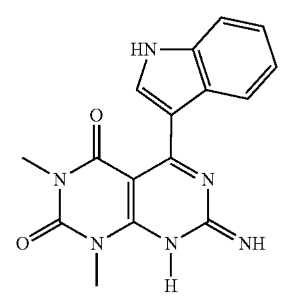 [SMILES: Cn1c(=O)c2c(-c3c[nH]c4ccccc34)nc(=N)[nH]c2n(C)c1=O] | 98 ± 1.53 |

It is to be understood that the 7-imino-5-(1H-indol-3-yl)-1,3-substituted-7,8-dihydropyrimido[4,5-d]pyrimidine-2,4(1H,3H)-dione derivatives are not limited to the specific

We claim:

1. A compound having the formula I:

[Chemical structure of Formula I showing indole connected to a pyrimido[4,5-d]pyrimidine core with R¹, R², Y, and NH substituents]

I or a pharmaceutically acceptable salt, wherein:
R¹ is selected from the group consisting of hydrogen and methyl;
R² is selected from the group consisting of hydrogen and methyl; and
Y is selected from the group consisting of O and S.

2. The compound of claim 1, wherein R¹ and R² are both hydrogen.

3. The compound of claim 2, wherein Y is O or S.

4. The compound of claim 1, wherein R¹ and R² are both methyl.

5. The compound of claim 4, wherein Y is O.

6. The compound of claim 1, wherein the compound is selected from the group consisting of:
7-Imino-5-(1H-indol-3-yl)-7,8-dihydropyrimido[4,5-d]pyrimidine-2,4(1H,3H)-dione (4a),
7-Imino-5-(1H-indol-3-yl)-2-thioxo-2,3,7,8-tetrahydropyrimido[4,5-d]pyrimidin-4(1H)-one (4b),
7-Imino-5-(1H-indol-3-yl)-1,3-dimethyl-7,8-dihydropyrimido[4,5-d]pyrimidine-2,4(1H,3H)-dione (4c),
and a pharmaceutically acceptable salt.

7. A pharmaceutically acceptable composition comprising a therapeutically effective amount of the compound of claim 1 and a pharmaceutically acceptable carrier.

8. A method of inhibiting COX-2 enzyme activity in a patient, comprising administering to a patient in need thereof a therapeutically effective amount of the compound of claim 1.

9. A method of reducing inflammation in a patient, comprising administering to a patient in need thereof a therapeutically effective amount of the compound of claim 1.

10. A compound having the formula I:

[Chemical structure of Formula I]

I or a pharmaceutically acceptable salt, wherein:
R¹ and R² are both hydrogen or are both methyl; and
Y is selected from the group consisting of O and S.

11. A pharmaceutically acceptable composition comprising a therapeutically effective amount of the compound of claim 10 and a pharmaceutically acceptable carrier.

12. A method of inhibiting COX-2 enzyme activity in a patient, comprising administering to a patient in need thereof a therapeutically effective amount of the compound of claim 10.

13. A method of reducing inflammation in a patient, comprising administering to a patient in need thereof a therapeutically effective amount of the compound of claim 10.

14. A compound selected from the group consisting of:
7-Imino-5-(1H-indol-3-yl)-7,8-dihydropyrimido[4,5-d]pyrimidine-2,4(1H,3H)-dione (4a),
7-Imino-5-(1H-indol-3-yl)-2-thioxo-2,3,7,8-tetrahydropyrimido[4,5-d]pyrimidin-4(1H)-one (4b),
7-Imino-5-(1H-indol-3-yl)-1,3-dimethyl-7,8-dihydropyrimido[4,5-d]pyrimidine-2,4(1H,3H)-dione (4c),
and a pharmaceutically acceptable salt.

15. A pharmaceutically acceptable composition comprising a therapeutically effective amount of the compound of claim 14 and a pharmaceutically acceptable carrier.

16. A method of inhibiting COX-2 enzyme activity in a patient, comprising administering to a patient in need thereof a therapeutically effective amount of the compound of claim 14.

17. A method of reducing inflammation in a patient, comprising administering to a patient in need thereof a therapeutically effective amount of the compound of claim 14.

* * * * *